United States Patent
Ahn et al.

(10) Patent No.: US 7,192,571 B2
(45) Date of Patent: Mar. 20, 2007

(54) ANTI CALCULUS AND PLAQUE TOOTHPASTE COMPOSITION

(75) Inventors: Jae-Hyun Ahn, Daejeon (KR);
Jin-Hwan Lee, Daejeon (KR);
Taek-Kyun Kang, Daejeon (KR);
Young-Ho Kim, Daejeon (KR)

(73) Assignee: LG Household & Health Care Ltd., Seoul (KR)

( * ) Notice: Subject to any disclaimer, the term of this patent is extended or adjusted under 35 U.S.C. 154(b) by 344 days.

(21) Appl. No.: 10/450,016

(22) PCT Filed: Dec. 6, 2001

(86) PCT No.: PCT/KR01/02112

§ 371 (c)(1),
(2), (4) Date: Jun. 6, 2003

(87) PCT Pub. No.: WO02/45677

PCT Pub. Date: Jun. 13, 2002

(65) Prior Publication Data

US 2004/0033204 A1    Feb. 19, 2004

(30) Foreign Application Priority Data

Dec. 8, 2000  (KR) ............................ 2000-74600

(51) Int. Cl.
*A61Q 11/00*      (2006.01)
*A61K 8/00*       (2006.01)

(52) U.S. Cl. ........................... 424/49; 424/57; 424/684

(58) Field of Classification Search ............ None
See application file for complete search history.

(56) References Cited

U.S. PATENT DOCUMENTS 4,871,396 A  * 10/1989  Tsujita et al. ............ 106/286.8
4,913,895 A  *  4/1990  Miyake et al. ................ 424/57
5,094,844 A     3/1992  Gaffar et al.

FOREIGN PATENT DOCUMENTS

| KR | 1991-2096 B1 | 4/1991 |
| KR | 1999-16248 A | 3/1999 |
| KR | 10-0221157 B1 | 9/1999 |

OTHER PUBLICATIONS

American Academy of Periodontology, http://www.perio.org/consumer/faq_general.htm, pp. 1-4 Oct. 2004.*
American Dental Association http://www.ada.org/public/topics/plaque.asp pp. 1-2 Oct. 2003.*
NIDCR/NIH, Plaque: what it is and how to get rid of it, http://www.nidcr.nih.gov/NR/rdonlyres/DB2E21FD-E8CD-4C1D-B50F-775AC01EF11F/0/Plaque_brochure.pdf, pp. 1-2 Jul. 1999.*

* cited by examiner

Primary Examiner—Frederick Krass
Assistant Examiner—Lezah Roberts
(74) Attorney, Agent, or Firm—Alston & Bird LLP

(57) ABSTRACT

The present invention relates to a toothpaste composition for preventing calculus formation and removing plaque, more specifically to the toothpaste composition comprising soluble ultra phosphate with network structure and zeolite granule. The composition of the present invention has superior effect to prevent and remove calculus, and removing interdental plaque.

6 Claims, No Drawings

ANTI CALCULUS AND PLAQUE TOOTHPASTE COMPOSITION

BACKGROUND OF THE INVENTION (a) Field of the Invention

The present invention relates to a toothpaste composition having excellent effects for removing calculus and bacterial film on dental surface (hereinafter referred to as "plaque"). More specifically, the present invention relates to a toothpaste composition having excellent effects for removing interdental plaque and calculus and preventing calculus formation by comprising zeolite granule and ultra phosphate.

(b) Description of the Related Art

Generally, plaque is adhesive material made by bacteria in the oral cavity such as *Streptococcus mutans*, etc., which is adhered to dental surface or gingiva and causes dental caries in the oral cavity and gingivitis. If such plaque is not removed and is left for a long time, calcification will slowly proceed and it will turn into blackish brown calculus. Calculus is hard and stiff material formed around tooth. The calculus begins to be formed when unremoved plaque reacts with metal ions such as calcium ion, magnesium ion, etc. contained in foods and saliva and is deposited and crystallized. Such calculus is difficult to remove by common tooth-brushing. If it does not removed, it grows into the neck of the tooth and causes various paradentitis.

The mechanism of calculus formation has not completely clarified, and although slightly varies according to various known technologies, U.S. Pat. No. 4,138,477 and British Patent Nos. 2,182,242 and 2,180,157 explain the mechanism as growing into crystalline material named hydroxyapatite (HAP) of calcium and orthphosphate. Accordingly, material that can block functions of calcium, main ingredient of crystalline hydoxyapatite, can be effective anti-calculus agent, and if calculus-causing material, plaque, can be completely removed, the formation of calculus can be basically blocked. However, complete removal of plaque is practically impossible and although dental surface plaque can be removed by common toothpaste, the removal of plaque in the parts where teeth-brushing does not reach well such as between teeth and teeth and between teeth and gingiva is very difficult.

Meanwhile, it is known that although hydroxyapatite, main ingredient of calculus, is similar to ingredient of teeth, they differ completely in their crystalline structure and differ greatly in their hardness. However, it should be noted that the use of excessive anti-calculus ingredient could affect tooth enamel as well as calculus.

Main ingredient of calculus is hydroxyapatite, which has the same composition as main ingredient of tooth and they differ only in their structural fineness. Water-soluble metal ion condensed phosphate having linear molecular structure has been proved its effects as an anti-calculus agent through various studies and clinical tests. Particularly, hexamethaphosphate, tripolyphosphate, pyrophosphate, etc. have been used for a toothpaste composition, which are also known as chelating agents. It is known that they have functions for chelating, inhibiting and isolating calcium, magnesium, ferrous ions, etc., and that they inhibit calcium ion that is indispensable for forming crystalline hydroxyapatite and thus effectively prevent calculus.

U.S. Pat. No. 4,515,772 and British Patent Nos. 2,182,244 and 2,180,157 have disclosed water-soluble condensed phosphate having linear molecular structure such as dialkali metal pyrophosphate or alkali metal pyrophosphate, tripolyphosphate, hexamethaphosphate as anticalculus agents. Besides such water-soluble alkali metal condensed phosphate having linear molecular structure, U.S. Pat. No. 4,138,477 has suggested vinylmethylether/maleic acid copolymer (PVM/MA) as an anticalculus agent, which has been clarified to increase anti-calculus effects of water-soluble condensed phosphate having linear molecular structure.

However, the toothpaste compositions disclosed in the above patents have problems in use feels due to salty taste and unique teeth-brushing feels of phosphate because they use excessive alkali metal condensed phosphates, and they focus on chelating effects for calcium ions affecting calculus-formation and do not consider any influence on tooth enamel that is structural ingredient of tooth.

Korean Parent Publication No. 1991-0002096 has disclosed the use of water-soluble alkali metal condensed phosphate with network molecular structure having excellent anti-calculus effects, sodium citrate having synergistic effects wit the condensed phosphate, and fluoring compound commonly used in toothpaste in order to inhibit hydrolysis of condensed phosphate with the lapse of time, but it cannot completely inhibit hydrolysis of condensed phosphate with the lapse of time at high temperature. As disclosed in Korean Patent Publication No. 1991-0002096, the water-soluble alkali metal condensed phosphate having the network molecular structure is referred to as ultraphosphate, and is expressed as the following formula:

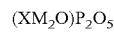

$$(XM_2O)P_2O_5$$

wherein X represents a number from 0 to 1, and M represents an alkali metal. Differently from the case that the ratio of $P_2O_5:M_2O$ ranges from 1:1 to 1:2, it is presumed in the case of the ultraphosphate that more condensations occur, to form a three-dimensional network structure. Because the ultraphosphate is amorphous, the individual structure of the ultraphosphate cannot be clearly determined by X-ray diffraction. However, it is reported that the ultraphosphate has a network structure, based on the presence of various ion species in the aqueous solution and the change thereof depending on the elapsed time measured by a paper chromatography.

Meanwhile, as technologies for removing plaque, a conventional method of prescribing highly polishing toothpaste and a method of using antibacterial that inhibits multiplication of plaque-making bacteria have been generally used, but the use of highly polishing toothpaste would cause chilled teeth due to abrasion of teeth and, when used for a long time, gingival abrasion, and the use of antibacterial has a problem of bacteria resistance. Recently, Japanese Patent No. 61-280331 and Korean Patent Publication No. 1992-5641 have used plaque-decomposable enzymes in toothpaste and Japanese Patent 61-280331 and Korean Patent Publication No. 1997-121564 have granulated insoluble inorganic matter to apply it to a toothpaste thereby increasing tooth whitening and polish, but they cannot ultimately remove interdental plaque and do not consider dental stability.

Accordingly, there is a need for a toothpaste composition having excellent anti-calculus and interdental plaque removal effects as well as having tooth enamel stability.

SUMMARY OF THE INVENTION

The present invention is made in order to solve these problems of the prior art, and as results of various studies about novel material and synergism of the existing material focusing on complete plaque-removal, prevention and removal of calculus-formation and whether or not tooth enamel is damaged, the present inventors have discovered a toothpaste composition which exhibits excellent laboratorial and clinical effects, is safe to human body and stable with the lapse of time, and have completed the present invention.

Accordingly, it is an object of the present invention to provide a toothpaste composition having excellent anti-calculus and interdental plaque-removal effects as well as having tooth enamel stability.

DETAILED DESCRIPTION AND THE PREFERRED EMBODIMENTS

In order to achieve these objects, the present invention provides a toothpaste composition for preventing calculus and removing interdental plaque, characterized by comprising water-soluble alkali metal condensed phosphate with network molecular structure as an anticalculus agent and granules prepared by mixing zeolite and silica in a specific ratio.

Generally, a condensed phosphate is divided according to the ratio of $M_2O/P_2O_5$. (M: alkali metal), which is divided into ultra phosphate when the ratio is less than 1, polyphosphate when the ratio is more than 1, and metaphosphate when the ratio is close to 1. In the present invention, ultra phosphate having a network molecular structure with the ratio of $M_2O/P_2O_5$ of less than 1 is used, which has stronger and-calculus effects than the existing water-soluble condensed phosphates with linear molecular structures, metaphosphate, phyrophostate, and polyphosphate.

It is preferable to use sodium ultra metaphosphate or acidic sodium polyphosphate as the condensed phosphate in the present invention.

The condensed phosphate is preferably contained in an amount of 0.1 to 5 wt % of the total composition. When the contents of the condensed phosphate are less than 0.1 wt %, calculus formation preventing effects will be insignificant, and when the contents are more than 5 wt %, hardness of tooth enamel may decrease due to excessive anti-calculus effects and use feels are not good because of the unique taste of phosphate.

However, the condensed phosphate is rapidly hydrolyzed with the lapse of time particularly at high temperature. Accordingly, the present invention exhibits hydrolysis preventing effects as well as excellent calculus-preventing and removal effects by using granules prepared by mixing zeolite, silica and titanium dioxide. In addition, such granule increases interdental plaque-removal effects due to its physicochemical properties, it is safe to tooth enamel and strengthens tooth together with fluorine ingredient.

The granule of the present invention acts to prevent the hydrolysis of condensed phosphate and remove interdental plaque. The granule is preferably contained in an amount of 0.2 to 10 wt % of the total composition. If the contents are less than 0.2 wt %, the hydrolysispreventing effects will be insignificant, and Kf the contents are more than 10 wt %, use feels will be poor due to excessive use of granule and costs will increase.

Preferably, the zeolite granule in the present invention comprises 80 to 99 wt% of zeolite, 0.5 to 10 wt % of silica and 0.5 to 10 wt % of titanium dioxide, and it is prepared using granulator (for example, rotary type granulator). The zeolite, silica and titanium dioxide include all the compounds that can be used in a toothpaste composition and preferably the zeolite is sodium aluminosilicate and silica is precipitated silica.

When applying said granule to an ointment type toothpaste, the size and strength of the granule should be appropriately determined according to use feels of consumers and manufacturing process. If the strength of the granule is too high, tooth might be damaged and interdental plaque removing effects might decrease because the granule would not be broken during teeth-brushing. In addition, if the strength of the granule is too low, the granule might be broken during toothpaste manufacturing process. A breaking strength is preferably 150 to 650 $g/cm^2$, and the size is preferably is 100 to 800 μm. The strength of the above range is such that the granule is broken by the strength applied by common teeth-brushing and it is not broken during manufacturing process, and the size of the above range is to exhibit appropriate use feels and interdental plaque removing effects.

The composition of the present invention includes any ingredients that can be used as a vehicle in a toothpaste composition. Generally, although not limited hereto, vehicles include a polishing agent, a wetting agent, a binding agent, a foaming agent, a flavor, a sweetening agent, a pigment, a pH controlling agent, etc.

The toothpaste composition of the present invention can include a polishing agent. The polishing agent is preferably selected from a group consisting of precipitated silica, silica gel, zirconium silicate, dicalcium phosphate dihydrate, dicalcium phosphate anhydrate, hydrated alumina, hard calcium carbonate, moderate calcium carbonate, calcium pyrophosphate, insoluble metaphosphate, aluminum silicate and a mixture thereof, and the contents thereof are preferably 5 to 60 wt %. The average particle diameter of the polishing agent is, although varied according to the kinds thereof, preferably 20 μm or less. Although any standard regarding teeth-polishing degree has not been established, generally toothpastes having polishing degree below 50 is divided into low polishing toothpaste, those having polishing degree of 50 to 100 is divided into medium polishing toothpaste, and those having polishing degree over 100 is divided into high polishing toothpaste, and teeth-brushing with a high polishing toothpaste for a long time could cause gingival abrasion. Such a polishing degree of toothpaste is determined by the kind and contents of a polishing agent. The present invention uses the above-mentioned kinds of polishing agent in the above-mentioned range thereby making the polishing degree of the final product 50 to 100.

The toothpaste composition of the present invention may further include a wetting agent. A wetting agent is indispensable base ingredient for making ointment type preparations, which prevents drying and solidification of a toothpaste when exposed into the air, provides gloss on toothpaste surface and gives sweetening effects when teeth-brushing according to its kind. The wetting agent used in the present invention is preferably selected from a group consisting of concentrated glycerine (98%), glycerine (85%), sorbitol solution (70%), noncrystalline sorbitol solution (70%), xylitol, polyethylene glycols, propylene glycols and a mixture thereof, and the contents thereof are preferably 20 to 70 wt %.

In addition, the toothpaste composition of the present invention may further comprise medicinal ingredients. Common toothpaste compositions comprise appropriate medicinal ingredients according to use purpose, and recently fluorides that form fluorine films on tooth to make tooth resistant to acids such as lactic acids, metabolites of dental caries-causing bacteria, are recognized to be indispensable for a toothpaste composition. The present invention preferably uses sodium fluoride or sodium monofluoro phosphate alone or in combination, and it is preferable to use 1,000 ppm or less of fluoride ions allowed in Korean Pharmaceutical Laws (in case of sodium fluoride, 0.22%, in case of sodium monofluoro phosphate, 0.76%). In addition, in order to prevent paradentitis, water-soluble salts such as sodium chloride, sodium bicarbonate having high osmotic pressure, aminocaproic acid, alantoin and alantoin derivatives and various vitamins can be simultaneously used.

In addition, the toothpaste composition of the present invention may further comprise a binding agent. A binding agent, which prevents separation of solid powder ingredients and liquid ingredients, is indispensable for an ointment type toothpaste, and any water-soluble macromolecules can be used. Sodium carboxymethyl cellulose synthesized from cellulose of trees, carrageenan extracted from sea-weeds and xanthan gum obtained from metabolism of microorganisms, etc. are generally used.

In addition, the toothpaste composition of the present invention may further comprise a foaming agent. A foaming agent increases use feels of product, aids cleaning and facilitates dispersion and penetration of medicinal ingredients and decreases surface tension thereby easily separating extraneous matter. As a foaming agent, anionic surfactant sodium lauryl sulfate is predominantly used, and nonionic surfactant polyoxyethylene polyoxypropylene copolymer (poloxamer), polyoxyethylene hardened castor oil, polyoxyethylene sorbitan fatty acid ester, etc. can be supplementarily used according to the properties of preparations.

In addition, in order to enhance use feels of the toothpaste composition, the toothpaste composition of the present invention may comprise a flavor, a sweetening agent, a pigment, etc. As the flavors, edible flavors must be used, and peppermint oil, spearmint oil, sage, eucalyptol, methylsalycilate and fruit extracts can be used. As the sweetening agent, sodium saccharine is commonly used and as the pigments, edible pigments are used.

The present invention will be explained in more detail with reference to the following Examples and Comparative Examples. However, the following examples are for illustration of the present invention, and the present invention is not limited to them.

EXAMPLE

Examples 1–4 and Comparative Examples 1–4

The toothpaste compositions of the present invention (Examples 1 to 4) and the existing toothpaste compositions (Comparative Examples 1 to 4) were prepared with compositions as shown in Tables 1a and 1b by the following process.

1) A binding agent and other additives were previously dispersed in a wetting agent, a polishing agent and medicinal agents such as an anti-calculus agent were injected therein, and the mixture was agitated for approximately 30 minutes.
2) After injecting a foaming agent and a flavor, the mixture was agitated for 20 minutes under vacuum to obtain a final product.

TABLE 1a

| | | Example | | | | Comparative Example | | | |
| --- | --- | --- | --- | --- | --- | --- | --- | --- | --- |
| | Ingredient | 1 | 2 | 3 | 4 | 1 | 2 | 3 | 4ᵉ |
| Polishing Agent | Precipitated Silica | 20.0 | — | 5.0 | — | — | 20.0 | 20.0 | — |
| | Dicalcium Phosphate dihydrate | — | 40.0 | — | — | — | — | — | 40.0 |
| | Hydrated Alumina | — | — | — | 30.0 | 30.0 | — | — | 3.0 |
| | Calcium Carbonate | — | — | 35.0 | 5.0 | 5.0 | — | — | — |
| | Calcium Pyrophosphate | — | — | — | 5.0 | 5.0 | — | — | — |
| | Silica Gel | — | 3.0 | — | — | — | — | — | — |
| Wetting Agent | Concentrated Glycerin (98%) | — | 30.0 | 20.0 | — | — | — | 20.0 | — |
| | Sorbitol Aqueous Solution (70%) | 50.0 | — | — | 30.0 | 30.0 | 50.0 | 30.0 | 35.0 |
| | Xylitol | — | — | 5.0 | 1.0 | 1.0 | — | — | — |
| Foaming Agent | Sodium Lauryl Sulfate | 2.0 | 2.0 | 2.0 | 2.0 | 2.0 | 2.0 | 2.0 | 2.0 |
| | Poloxamer | — | — | 0.5 | — | — | — | — | — |
| Binding Agent | Sodium Carboxymethyl Cellulose | 0.2 | 0.4 | — | — | — | — | 0.8 | — |
| | Xanthan Gum | 0.5 | — | 0.8 | 0.2 | 0.2 | 0.6 | — | — |
| | Carrageenan Gum | — | 0.5 | — | 0.5 | 0.5 | — | — | 1.0 |

TABLE 1b

| | Ingredient | Example 1 | Example 2 | Example 3 | Example 4 | Comparative Example 1 | Comparative Example 2 | Comparative Example 3 | Comparative Example 4[c] |
|---|---|---|---|---|---|---|---|---|---|
| Calculus and Palque Preventing Agent | Network-type Condensed Phosphate[a] | 1.0 | 2.0 | 3.0 | 5.0 | 5.0 | — | — | — |
| | Zeolite Granule[b] | 3.0 | 10.0 | 5.0 | 2.0 | — | — | — | — |
| | Sodium Pyrophosphate | — | — | — | — | — | 2.4 | 3.5 | — |
| | Potassium Pyrophosphate | — | — | — | — | — | 2.36 | 4.5 | — |
| | Acidic Sodium Pyrophosphate | — | — | — | — | — | 1.19 | — | — |
| | Vinyl Methylether/ Maleic Acid Copolymer | — | — | — | — | — | — | 2.0 | — |
| | Dextranase (500,000 units/g) | — | — | — | — | — | — | — | 0.5 |
| Fluorine | Sodium fluoride | — | 0.22 | 0.22 | 0.11 | 0.11 | 0.22 | 0.22 | — |
| | Sodium monofluoro phosphate | 0.76 | — | — | 0.38 | 0.38 | — | — | 0.76 |
| Additives | Flavor | 1.0 | 1.0 | 1.0 | 1.0 | 1.0 | 1.0 | 1.0 | 1.0 |
| | Sodium Saccharine | 0.1 | 0.1 | 0.1 | 0.1 | 0.1 | 0.1 | 0.1 | 0.1 |
| | Purified Water | 21.44 | 10.78 | 22.38 | 17.71 | 19.71 | 20.13 | 15.88 | 16.64 |

[a]Sporix, Seodo Chemical Company product, was used as network-type condensed phosphate.
[b]Colite, Cosmo Industry product, was used as zeolite granule.
[b]Enzymes of 500,000 units/g were used In an amount of 0.5% of the toothpaste, and enzyme titer per toothpaste gram is 2,500 units/toothpaste gram.

Example 5 and Comparative Example 5

Evaluation of Laboratorial Anti-calculus Effects

In order to compare laboratorial anti-calculus effects, anti-calculus effects were compared and evaluated through chelating test for calcium ions, main ingredient of calculus.

Each 100 g of the compositions of Examples 1 to 4 and Comparative Examples 1 to 4 were taken and water was added thereto. Then, the mixture was centrifuged at 10,000 rpm for 30 minutes and supernatant was gathered. And 5.0 ml of saturated ammonium oxalate was added thereto and the mixture was titrated using standard calcium solution until the first permanent white precipitation was produced. Chelation value for chelated calcium ions was calculated from consumed ml of standard calcium solution, and the results are shown in Table 2.

Chelation Value =

$$\frac{\text{Consumption of Standard Calcium Solution (ml)} \times 50.0}{\text{Contents of Anti-calculus Agent in Sample (g)}}$$

The value 50.00 in the above formula is mg of $CaCO_3$ per 1 ml of standard calcium solution.

As shown in Table 2, the compositions of Examples exhibited much higher calcium ion chelation value than those of Comparative Examples.

Example 6 and Comparative Example 6

Evaluation of Laboratorial Calculus-Removal Effects

In order to confirm calculus-removal effects, real calculus was gathered from patients needed scaling and it was finely pulverized and dried, and specific amount thereof was taken. Toothpaste solutions with a ratio of toothpaste: water=1:3 were prepared using the toothpaste compositions of Examples 1 to 4 and Comparative Examples 2 to 3 and centrifuged and 5 ml of supernatant were taken. The calculus was soaked in the supernatant for 24 hours at 37° C., and then filtrated and dried to calculate calculus-removal rates from reduced weight of calculus.

TABLE 2

| | Example 1 | Example 2 | Example 3 | Example 4 | Comparative Example 2 | Comparative Example 3 |
|---|---|---|---|---|---|---|
| Chelation Value | 210 | 320 | 440 | 560 | 40 | 60 |

TABLE 3

| | Example 1 | Example 2 | Example 3 | Example 4 | Comparative Example 2 | Comparative Example 3 |
|---|---|---|---|---|---|---|
| Calculus-removal rat (%) | 25% | 33% | 38% | 43% | 18% | 17% |

As shown in Table 3, the compositions of Examples exhibited superior effects to those of Comparative Examples.

Example 7 and Comparative Example 7

Evaluation of Laboratorial Interdental Plaque Removal Effects

Artificial teeth similar to natural teeth was designed, and soaked in plaque-forming bacteria *Streptococcus mutans*-inoculated Brain Heart medium and 1% sucrose solution. And, it was cultivated at 37° C. for 48 hours to artificially adhere plaque. After removing medium, plaque-discerning agent was coated to confirm that plaque was entirely formed. And liquid diluted to 30% aqueous solution from toothpaste compositions of Examples 1 to 4 and Comparative Examples 1 to 4 were applied to each artificial teeth. Then, alternating motions were carried out on each artificial teeth 300 times using the same type toothbrushes with a pressure of 250 g/cm$^2$ commonly applied by teeth-brushing, and the teeth was cleaned with flowing water. Remaining interdental plaque was observed with the naked eyes, evaluated with the following standard and shown in Table 4.

Evaluation standard was as follows:
1: No interdental plaque
2: Small amount of interdental plaque remains (spot-shaped)
3: Interdental plaque remains (linear shaped)
4: Large amount of interdental plaque remains (face-shaped)
5: Plaque also remains on dental surface.

TABLE 4

| | Example | | | | Comparative Example | | | |
|---|---|---|---|---|---|---|---|---|
| | 1 | 2 | 3 | 4 | 1 | 2 | 3 | 4 |
| Evaluation Value for remaining plaque | 1.5 | 1.0 | 1.3 | 1.1 | 3.5 | 4.0 | 4.3 | 4.5 |

As shown in Table 4, the compositions of Examples exhibited superior interdental plaque removal effects to those of Comparative Examples.

Example 8 and Comparative Example 8

Evaluations of Clinical Calculus and Interdental Plaque Removal Effects

In order to clinically confirm calculus removal and interdental plaque removal effects of the compositions of Examples and Comparative Examples, 60 men and women of ages 20 to 40 having much calculus were elected and divided into three groups. And they were made to use simple fluorine toothpaste on the market for 1 week, and then calculus index and plaque index were recorded, which were set as baselines (initial indexes). After educating the same oral sanitary controlling method, each composition of Examples 4 and Comparative Examples 1 and 2 were provided to each group and used for 3 months. Then, calculus index (end calculus index value) and plaque index (end plaque index value) were evaluated and reduction rates were calculated from indexes before and after 3 month.

TABLE 5

$$\text{Calculus reduction rate (\%)} = \frac{\text{Initial Calculus Index} - \text{End Calculus Index}}{\text{Initial Calculus Index}} \times 100$$

$$\text{Plaque reduction rate (\%)} = \frac{\text{Initial Plaque Index} - \text{End Plaque Index}}{\text{Initial Plaque Index}} \times 100$$

| | Example 4 | Comparative Example 1 | Comparative Example 2 |
|---|---|---|---|
| Calculus Reduction Rate (%) | 31.5 | 13.4 | 8.3 |
| Plaque Reduction Rate (%) | 43.6 | 8.7 | 15.6 |

As shown in Table 5, the group using the composition of Example 4 exhibited statistically significant effects than groups using the compositions of Comparative Examples 1 and 2 in terms of both calculus removal and plaque removal effects (P<0.01).

Example 9 and Comparative Example 9

Evaluation of Laboratorial Tooth Enamel Stability

This is to examine whether anti-calculus agent damages the existing tooth enamel. Tooth extracted from healthy person of 20 to 30 ages were fixed to epoxy resin, and samples were manufactured such that the exposed area of the teeth sample is 2 mm×2 mm. And hardness was measured 6 times per each sample using Knoop Hardness tester to establish the average value as the initial hardness. After soaking each sample in the compositions of Examples 1 to 4 and Comparative Examples 1 to 4 for 2 minutes, the sample was cleaned with distilled water. After repeating this process four times a day for 2 weeks, the hardness of the sample was measured 6 times and the average value was set to the end hardness. Decalcification rate was calculated from the initial hardness and the end hardness, and the results are shown in Table 6.

TABLE 6

$$\text{Decalcification rate (\%)} = \frac{\text{Initial average hardness} - \text{End average hardness}}{\text{Initial average hardness}} \times 100$$

|  | Example | | | | Comparative Example | | | |
|---|---|---|---|---|---|---|---|---|
|  | 1 | 2 | 3 | 4 | 1 | 2 | 3 | 4 |
| Decalcification rate (%) | −23.1 | −20.0 | −10.2 | −12.4 | 12.7 | 24.3 | 21.5 | −1.8 |

As shown in Table 6, all the compositions of Examples exhibited minus values, which indicates that declacification did not occur and rather recalcification occurred to increase the hardness of tooth enamel.

Example 10 and Comparative Example 10

Evaluations of Time-Lapse Hydrolysis Stability of Anti-Calculus Ingredient Phosphate In order to evaluate time-lapse hydrolysis stability of the compositions of Examples 1 to 4 and Comparative Examples 1 to 3 using condensed phosphate, the degree of hydrolysis of condensed phosphate was evaluated by quantifying hydrolysis product orthophosphate using high speed liquid chromatography while storing the compositions at room temperature and 40° C.

TABLE 7

| Time-lapse | | Example | | | | Comparative Example | | |
|---|---|---|---|---|---|---|---|---|
|  |  | 1 | 2 | 3 | 4 | 1 | 2 | 3 |
| 6 months | Room Temperature | 10 ppm | 25 ppm | 30 ppm | 38 ppm | 2,500 ppm | 4,100 ppm | 3,400 ppm |
|  | 40° C. | 80 ppm | 133 ppm | 140 ppm | 146 ppm | 67,000 ppm | 53,000 ppm | 60,500 ppm |

As shown in Table 7, the compositions of Examples exhibited insignificant hydrolysis degree even after 6 months lapsed at 40° C.

Example 11 and Comparative Example 11

Evaluation of Stability of Toothpaste Composition

Stabilities of the toothpaste compositions of Examples 1 to 4 and Comparative Examples 1 to 4 were evaluated according to the following standard while storing the compositions at room temperature and 40° C.

<<Evaluation Standard>>
⊙ Very Good: Surface is smooth and no phase separation occurs.
◯ Relatively Good: Surface is a little rough and only opening part of tube is rather bad.
∇ Relatively Bad: Phase separation occurs and a little discoloration occurs.
× Very Bad: Phase separation seriously occurs and gas generation or hardening appears.

TABLE 8

| Time-lapse | | Example | | | | Comparative Example | | | |
|---|---|---|---|---|---|---|---|---|---|
|  |  | 1 | 2 | 3 | 4 | 1 | 2 | 3 | 4 |
| 1 month | Room Temperature | ⊙ | ⊙ | ⊙ | ⊙ | ⊙ | ⊙ | ⊙ | ⊙ |
|  | 40° C. | ⊙ | ⊙ | ⊙ | ⊙ | ⊙ | ⊙ | ⊙ | ◯ |
| 3 months | Room Temperature | ⊙ | ⊙ | ⊙ | ⊙ | ⊙ | ◯ | ⊙ | ∇ |
|  | 40° C. | ◯ | ⊙ | ◯ | ⊙ | ◯ | ◯ | ◯ | ∇ |
| 6 months | Room Temperature | ⊙ | ⊙ | ⊙ | ⊙ | ⊙ | ◯ | ◯ | ∇ |
|  | 40° C. | ∇ | ◯ | ◯ | ∇ | ∇ | ∇ | ∇ | × |
| 12 months | Room Temperature | ◯ | ◯ | ◯ | ◯ | ◯ | ∇ | × | × |
|  | 40° C. | ∇ | ∇ | ∇ | ∇ | × | × | × | × |

As shown in Table 8, the compositions of Examples were better in terms of time-lapse stability than those of Comparative Examples.

As can be seen from the results of the above experiments, comparing various effects and stabilities of the compositions of the present invention and the existing calculus preventing toothpastes and common plaque removing toothpastes, the toothpaste composition of the present invention is superior (See Table 2, 3, 4, 5 and 6), confirming that the intended effects were achieved.

As explained, the toothpaste composition of the present invention has excellent tooth enamel stability and time-lapse stability as well as excellent anti-calculus and plaque removal effects.

What is claimed is:
1. A toothpaste composition for removing plaque comprising:
   a) water-soluble alkali metal condensed phosphate with a network molecular structure; and
   b) zeolite granules containing 80 to 99 weight % of zeolite, 0.5 to 10 weight % of silica and 0.5 to 10 weight % of titanium dioxide,
   wherein the water-soluble alkali metal condensed phosphate with a network molecular structure has a ratio of $M_2O/P_2O_5$ of less than 1, wherein the size of the zeolite granule is 100 to 800 μm and the strength thereof is 150 to 650 g/cm².
2. The toothpaste composition according to claim 1, wherein the granule is contained in an amount of 0.2 to 10 wt % of the total composition.
3. The toothpaste composition according to claim 1, wherein the zeolite is sodium aluminosilicate.

4. The toothpaste composition according to claim 1, wherein the a) water-soluble alkali metal condensed phosphate is contained in an amount of 0.1 to 5 wt % of the total composition.

5. The toothpaste composition according claim 1, wherein the a) water-soluble alkali metal condensed phosphate is sodium ultra metaphosphate or acidic sodium polyphosphate.

6. The toothpaste composition according to claim 1, wherein the composition further comprises one or more vehicles selected from a group consisting of a polishing agent, a wetting agent, a binding agent, a foaming agent, a flavor, a sweetening agent, a pigment and a pH controlling agent.

* * * * *